(12) United States Patent
Ukita et al.

(10) Patent No.: US 6,577,701 B2
(45) Date of Patent: Jun. 10, 2003

(54) SECTION RECONSTRUCTION METHOD AND RADIOGRAPHIC APPARATUS

(75) Inventors: Masaaki Ukita, Kyoto (JP); Taketo Kishi, Osaka (JP); Shuhei Onishi, Ibaraki (JP); Eiichi Shintani, Uji (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 10/199,067

(22) Filed: Jul. 22, 2002

(65) Prior Publication Data

US 2003/0021373 A1 Jan. 30, 2003

(30) Foreign Application Priority Data

Jul. 30, 2001 (JP) ........................................ 2001-229317

(51) Int. Cl.$^7$ ................................................. A61B 6/03
(52) U.S. Cl. ............................... 378/4; 378/19; 378/901
(58) Field of Search ........................... 378/4, 8, 15, 19, 378/901

(56) References Cited

U.S. PATENT DOCUMENTS

2003/0021373 A1 * 1/2003 Ukita et al. .................... 378/4

OTHER PUBLICATIONS

Intel Architecture Optimization (Reference Manual); Copyright 1998, 1999 Intel Corporation; pp. 3–26 thru 3–29.

* cited by examiner

Primary Examiner—David V. Bruce
(74) Attorney, Agent, or Firm—Rader, Fishman & Grauer, PLLC

(57) ABSTRACT

An X-ray tube (X-ray focus) and an X-ray detector opposed to each other across an object synchronously scan the object to acquire radiographic data in each scan position. A section reconstruction method is provided in which the radiographic data or data resulting from a filtering process of the radiographic data is projected as back projection data back to a two-dimensional or three-dimensional reconstruction area virtually set to a region of interest of the object. Enlarged interpolation data is generated by interpolating the back projection data and then the enlarged interpolation data is projected back to the reconstruction area without interpolation. The number of interpolation computations is reduced to an amount corresponding to the enlargement by interpolation of the back projection data, to shorten the reconstruction computation time.

14 Claims, 8 Drawing Sheets

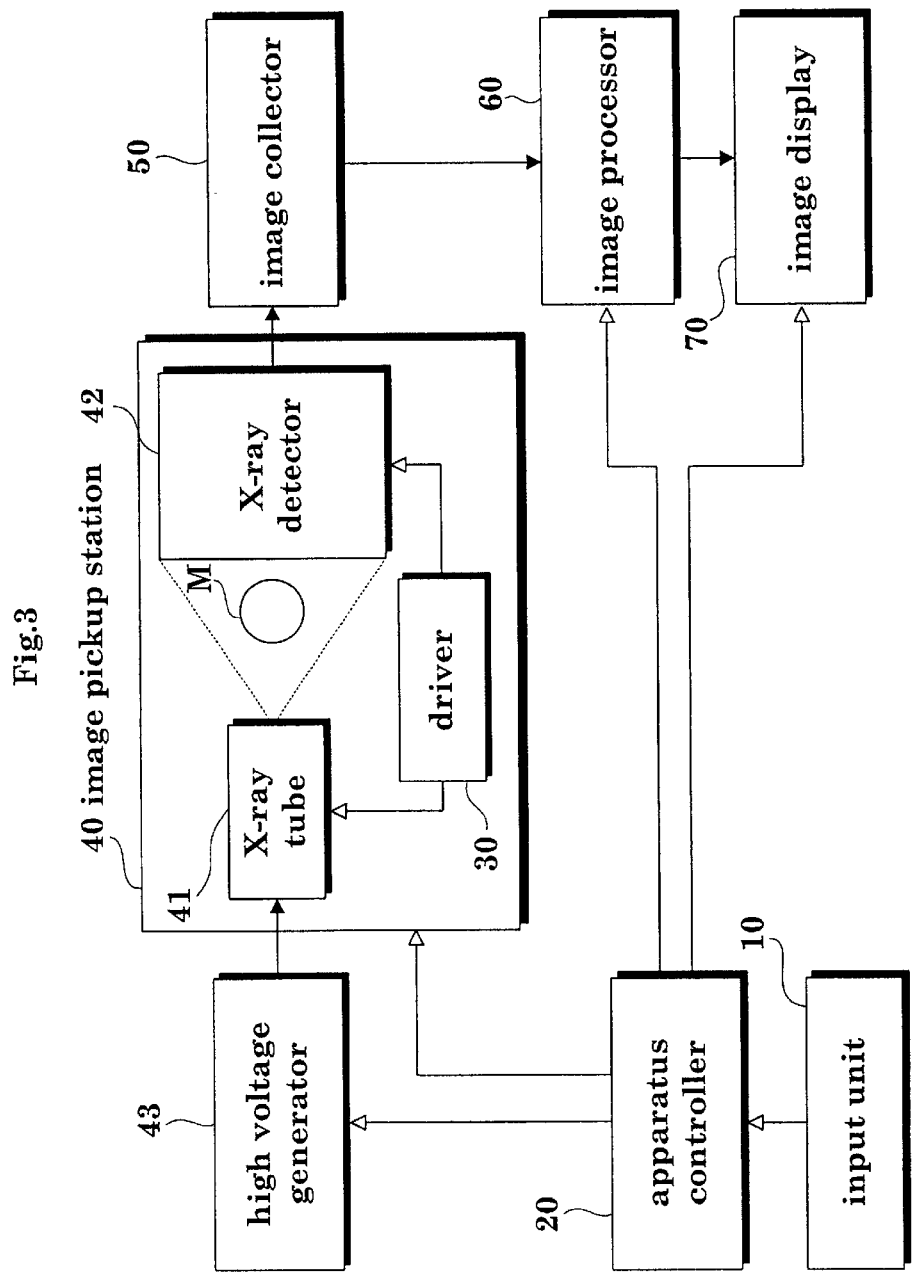

Fig.7

|  | prior art | | embodiment | | |
| --- | --- | --- | --- | --- | --- |
|  | equation (4) (1BP) | equation (4) ALL (all BPs) | equation(6) enlargement by interpolation in Procedure 1 | equation (9) (1BP) | equation(9) ALL (all BPs) | equation(6)+(9) (total computational complexity) |
| addition/ subtraction of integers | 1 | $1 \times n \times n \times Np$ | $1 \times L \times m \times Np$ | 0 | 0 | $1 \times L \times m \times Np$ |
| addition/ subtraction of floating decimals | 4 | $4 \times n \times n \times Np$ | $3 \times L \times m \times Np$ | 1 | $1 \times n \times n \times Np$ | $3 \times L \times m \times Np + n \times n \times Np$ |
| multiplication of floating decimals | 1 | $1 \times n \times n \times Np$ | $2 \times L \times m \times Np$ | 1 | $1 \times n \times n \times Np$ | $2 \times L \times m \times Np + n \times n \times Np$ |
| making floating decimals into integers | 1 | $1 \times n \times n \times Np$ | $1 \times L \times m \times Np$ | 1 | $1 \times n \times n \times Np$ | $1 \times L \times m \times Np + n \times n \times Np$ |
| reading back projection data | 2 | $2 \times n \times n \times Np$ | $2 \times L \times m \times Np$ | 1 | $1 \times n \times n \times Np$ | $2 \times L \times m \times Np + n \times n \times Np$ |
| reading/writing reconstruction points | 2 | $2 \times n \times n \times Np$ | 0 | 2 | $2 \times n \times n \times Np$ | $+ 2 \times n \times n \times Np$ |
| total number steps | 11 | $11 \times n \times n \times Np$ | $9 \times L \times m \times Np$ | 6 | $6 \times n \times n \times Np$ | $9 \times L \times m \times Np + 6 \times n \times n \times Np$ |

SECTION RECONSTRUCTION METHOD AND RADIOGRAPHIC APPARATUS

BACKGROUND OF THE INVENTION (1) Field of the Invention

This invention relates to section reconstruction methods for projecting radiographic data acquired in each scan position, or filtered radiographic data, as back projection data back to a reconstruction area, and various tomography apparatus for use in the medical, industrial and other fields for radiographing patients or objects under examination and reconstructing sectional images thereof. More particularly, the invention relates to a technique for speeding up the back projections in a reconstruction operation.

(2) Description of the Related Art

FIG. 1 shows a conventional X-ray tomography apparatus. The apparatus includes an X-ray focus f and an X-ray detector 42, with an array of X-ray detecting elements, opposed to each other across an object or patient. The X-ray focus f and X-ray detector 42 are rotatable synchronously around the object's body axis to radiograph the object intermittently from varied angles of X-ray emission to the object. Radiographic data acquired in each scan position is put to a reconstruction operation to reconstruct sectional images of the object.

As a reconstruction method, what is known as FBP (Filtered Back Projection) is often used. The FBP is a method in which radiographic data for a plurality (Np) of images of the object acquired from different scan positions is put to a filtering correction process to produce back projection data s which is projected back to a reconstruction area B virtually set to a site of interest of the object. To determine a pixel value of point b (x, y) in the reconstruction area B, for example, back projection data s (t (x, y, p)) of detector coordinates t (x, y, p) corresponding to a projection to point b (x, y) in a pth scan position is determined and added up the number of times Np. Thus, a total back projection to point b (x, y) is expressed by the following equation (1):

$$b(x, y) = \sum_{p=0}^{Np-1} s(t(x, y, p)) \quad (1)$$

Generally, various parameters are needed to compute detector coordinates t. However, since a scan position is determined by p, the detector coordinates corresponding to the projection to point (x, y) is regarded as t (x, y, p). Further, detector coordinates t (x, y, p) usually is not an integer, and therefore array data s cannot be determined directly. Floating-point interpolation computations are carried out using two adjacent points as shown in FIG. 2. In FIG. 2, u is an integer made by discarding fractional value a of t (x, y, p). An interpolation computation using (u, s (u)) and (u+1, s (u+1)) is expressed by the following equation (2):

$$b(x, y) = \sum_{p=0}^{Np-1} \{(1 - \alpha) \times s(u) + \alpha \times s(u + 1)\} \quad (2)$$

When a computer performs the above equation (2), a computation as expressed by the following equation (3) is carried out the number of projections (Np times):

$$b(x, y) = b(x, y) + (1-\alpha) \times s(u) + \alpha \times s(u+1) \quad (3)$$

Though the same computations as equation (3) above, the following equation (4) is actually used to reduce the number of computations:

$$b(x, y) = b(x, y) + \alpha \times (s(u+1) - s(u)) + s(u) \quad (4)$$

The above conventional computations has a disadvantage of involving numerous floating point computations, and thus takes a long time in performing reconstruction after a radiographic operation. Particularly, the interpolating computations with floating point in computing back projections are problematic. A floating point interpolation computational complexity will be described in detail.

First, of the computational expression (4) for one back projection to one point in a reconstruction area, computations for interpolation are listed below.

t→u making floating decimals of coordinates into integers ... one step u+1 adding integer to coordinates ... one step s (u), s (u+1) reading back projection data ... two steps α=t−u floating point computation of coordinates ... one step floating point multiplication of data ... one step floating point addition of data ... two steps The above computations provide interpolation data to be added to reconstruction point b (x, y). The interpolating computational complexity is eight steps in total. Next, one step is executed for reading b (x, y), then one step for floating point addition to the interpolation value, and finally one step for writing b (x, y) to complete the computations of equation (4). Thus, the computational complexity of equation (4) is 8+3=11 steps in total. The number of computational steps is shown in the column "equation (4) (1BP)" in FIG. 7.

The above equation (4) is repeated the number of times corresponding to the number of projections (Np times) to determine a reconstruction pixel value of one point b (x, y). Where the reconstruction area B includes n×n points, the computational complexity corresponding to equation (4) in all reconstruction computations becomes n×n×Np times. This computational complexity is shown in the column "Equation (4) ALL (all BP)" in FIG. 7. It will be seen that the total computational complexity in the prior art involves 11×n×n×Np steps, thus requiring a long time for the reconstruction computations.

SUMMARY OF THE INVENTION

This invention has been made having regard to the state of the art noted above, and its object is to provide a section reconstruction method and apparatus for speeding up a reconstruction operation.

To fulfill the above object, Inventor has made intensive research and attained the following findings. In the conventional reconstruction computation, data is interpolated in time of the back projection computations. It is time-consuming since the reconstruction requires a great number of floating-point interpolation computations proportional to a product of the number of times of projections Np and the number of section reconstruction pixels (e.g. n×n points). However, it has been found that interpolation computations repeatedly performed from back projection data far less than the reconstruction points include many similar interpolation computations which may be omitted.

In a solution Inventor has found based on this finding, enlarged interpolation data is obtained by enlarging back projection data by m times by interpolating, and thereafter the enlarged interpolation data is directly projected back to a reconstruction area without interpolation computation. In the back projection computation, the back projection data is selected from the enlarged interpolation data by determining by multiplying projection coordinates of reconstruction points by m. Where the enlargement-rate m is infinite, obviously the computations are the same as in the prior art. A finite enlargement-rate m will cause errors. However, by a suitable value m, excellent quality image is reconstructed and such reconstructed images present no problem. This solution reduces the number of interpolation computations to perform a fast reconstruction.

Based on the above finding, this invention provides section reconstruction methods for projecting radiographic data of an object acquired in each scan position back to a reconstruction area, the method comprising the step of generating enlarged interpolation data by interpolating back projection data and then projecting the enlarged interpolation data back to a two-dimensional or three-dimensional reconstruction area virtually set to a region of interest of the object, the back projection data being radiographic data, or data resulting from filtering of the radiographic data, the radiographic data being acquired in each scan position by causing a radiation source and a detector arranged opposite each other across the object to scan the object synchronously, or to scan the object synchronously with rotation of the object, the radiation source irradiating the object with electromagnetic waves capable of penetrating the object, the detector detecting electromagnetic waves transmitted through the object.

According to this invention, the number of interpolation computations is reduced to the amount corresponding to the enlargement computations by interpolating the back projection data, thereby reducing the section reconstruction computation time.

Preferably, the enlarged interpolation data is generated by an enlargement-rate set to an integer or decimal of at least 1.0. Then, the number of interpolation computations is reduced in proportion to the enlargement rate of the interpolation data, to shorten the reconstruction computation time.

Preferably, the enlarged interpolation data is generated by the enlargement-rate set to at least four times. With this arrangement, while securing an excellent quality of reconstructed images, the number of interpolation computations is reduced in proportion to the rate of enlargement by interpolation of the back projection data, to shorten the reconstruction computation time.

Preferably, when the reconstruction area is an enlarged reconstruction area subdivided to have pixel density exceeding a detector pixel density, the enlarged interpolation data is generated by an enlargement-rate variable in proportion to an enlargement-rate of an enlarged reconstruction area. Though the number of back projection points in the enlarged reconstruction area is increased, the number of interpolation computations hardly increases. As a result, in the case of enlarged reconstruction, the number of interpolation computations is drastically reduced to shorten the reconstruction computation time greatly.

Preferably, when a three-dimensional reconstruction is performed for projecting two-dimensional back projection data to the three-dimensional reconstruction area, two-dimensional enlarged interpolation data is generated by interpolating the two-dimensional back projection data, and the two-dimensional enlarged interpolation data is projected back to the three-dimensional reconstruction area. Even for a three-dimensional reconstruction, the number of interpolation computations is reduced in proportion to the rate of enlargement by interpolating the two-dimensional back projection data, to shorten the reconstruction computation time.

Preferably, the back projection data is enlarged by interpolation by an enlargement-rate variable with directions of back projection. This is effective to prevent quality deterioration in reconstructed images caused by the directions of back projection not parallel to the arrangement of pixels (back projection points) in the section reconstruction area.

Preferably, when the reconstruction area is a reduced reconstruction area reduced to have pixel density less than a detector pixel density, average interpolation data generated by interpolation after taking a moving average of the back projection data is projected back to the reduced reconstruction area. Then, an interpolation process following a moving average of the back projection data provides a fast, reduced reconstruction image while avoiding deterioration in the quality of the reduced reconstruction image. This allows results of the reconstruction to be known quickly.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

FIG. 3 is a block diagram of an X-ray radiographic apparatus in one embodiment of this invention;

FIG. 7 is a view showing a comparison in back projection computational complexity between the embodiment and the prior art;

DESCRIPTION OF THE PREFERRED EMBODIMENTS

Figure 1:
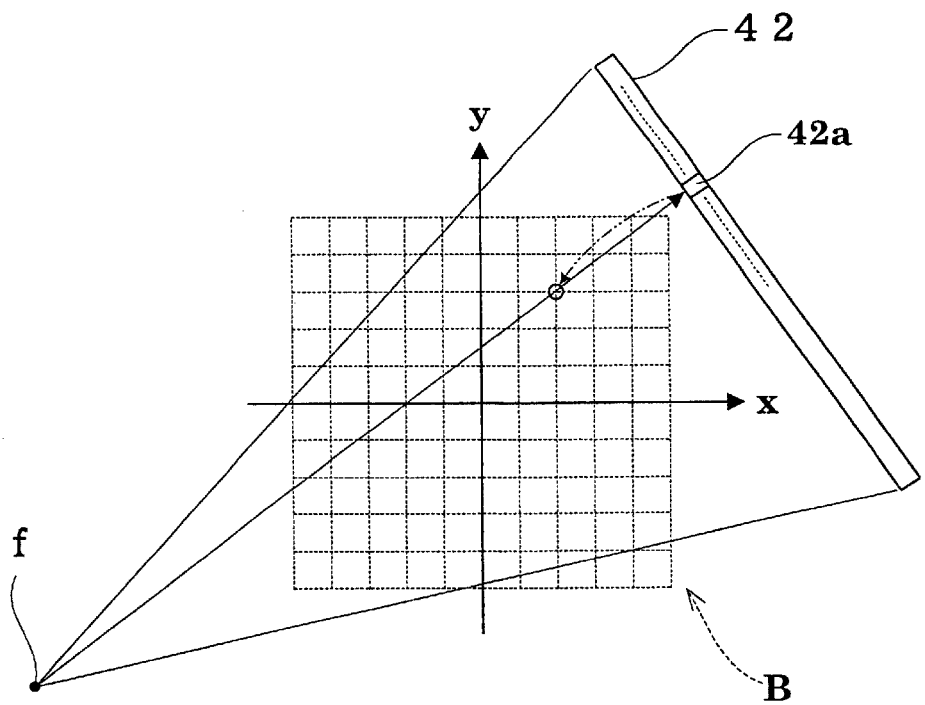
FIG. 1 is a schematic view illustrating a back projection to a section reconstruction area.
Figure 2:
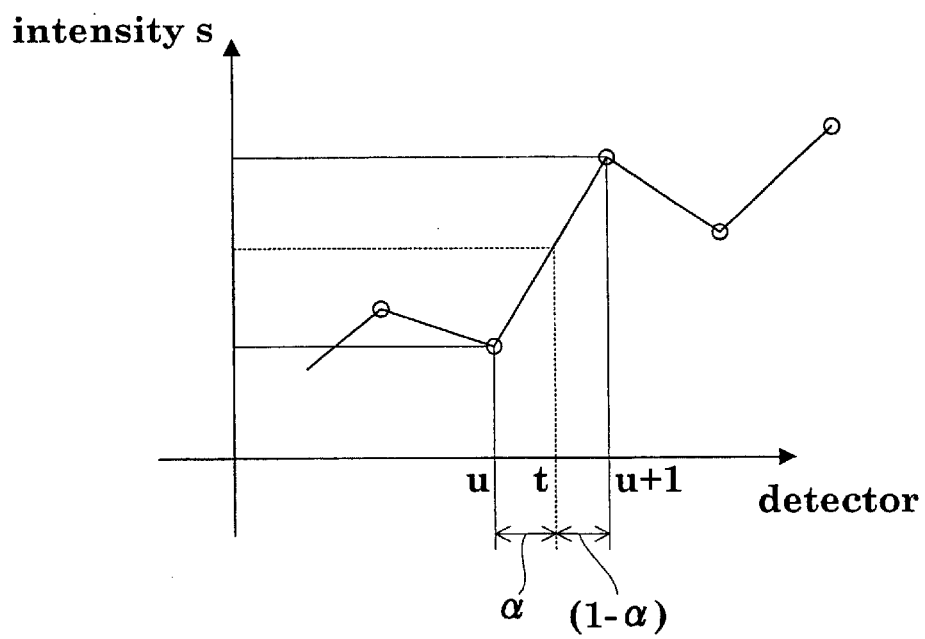
FIG. 2 is an explanatory view illustrating an interpolation for data detected by an X-ray detector.

A preferred embodiment of this invention will be described in detail hereinafter with reference to the drawings.

FIG. 3 is a block diagram of an X-ray radiographic apparatus, which is one example of radiographic apparatus according to this invention. This X-ray radiographic apparatus includes an input unit 10 for inputting various information and instructions, an apparatus controller 20 for controlling the entire apparatus such as its X-ray radiographic operation based on the information and instructions inputted, a driver 30 for operating an image pickup station 40 under control of the apparatus controller 20, the image pickup station 40 for acquiring images of a region of interest of an object M, an image collector 50 for collecting image information acquired by the image pickup station 40, an image processor 60 for performing a predetermined image processing such as an image reconstruction to generate and store sectional images of the region of interest of object M from image information provided by the image collector 50, and an image display 70 for displaying image information processed by the image processor 60. The image pickup station 40 includes an X-ray tube 41 for irradiating the object M with X rays, and an X-ray detector 42 for detecting X rays transmitted through the object M. The X-ray tube 41 is supplied with a necessary source voltage such as a tube current or tube voltage by a high voltage generator 43. With a collimator and a slit provided, the X-ray tube 41 irradiates the object M with X rays in a fan beam or cone beam.

The apparatus controller 20, which controls the entire radiographic apparatus, is in the form of dedicated hardware, workstation or personal computer storing apparatus controlling and computing methods, for example. The input unit 10 (e.g. a keyboard, mouse or buttons) connected to the apparatus controller 20 is operable by a user to collect and display various X-ray data. For example, the X-ray tube 41 and high voltage generator 43 are controlled to generate X rays, and at the same time X rays transmitted through the object M are converted into electric signals by the X-ray detector 42. Thereafter, the image collector 50 performs an AD (analog-to-digital) conversion of the electric signals to produce X-ray transmission data. The image processor 60 performs an image processing such as sensitivity or distortion correction on the X-ray transmission data, and then displays the data on the image display 70 (e.g. CRT or liquid crystal display) as appropriate.

In time of radiography, the object M is scanned, while the X-ray tube 41 and X-ray detector 42, or the object M, are/is moved mechanically to acquire numerous desired X-ray transmission data, thereby collecting radiographic data. It is the image pickup station 40 that determines features in outward appearance of the radiographic apparatus for linear scanning, two-dimensional CT (Computed Tomography), three-dimensional CT or spiral CT. The image pickup station 40 has a mechanical construction variable with a section reconstruction method. Section reconstruction computations according to this section reconstruction method are performed as part of the functions of the image processor 60 in the form of dedicated hardware or software using a DSP (digital signal processor). The image processor 60 corresponds to the image processing means of this invention.

Figure 4A:
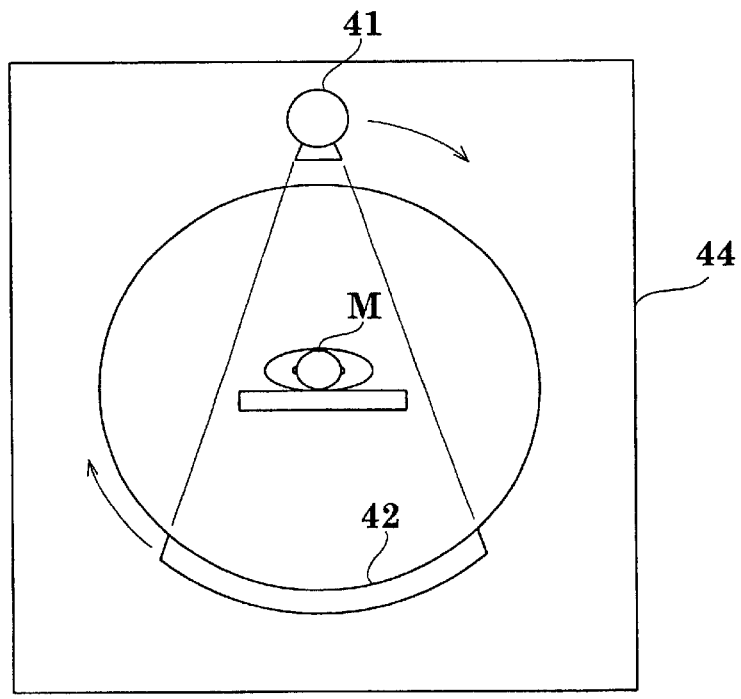
FIG. 4A is a schematic view of one example of image pickup station of the X-ray radiographic apparatus.
Figure 4B:
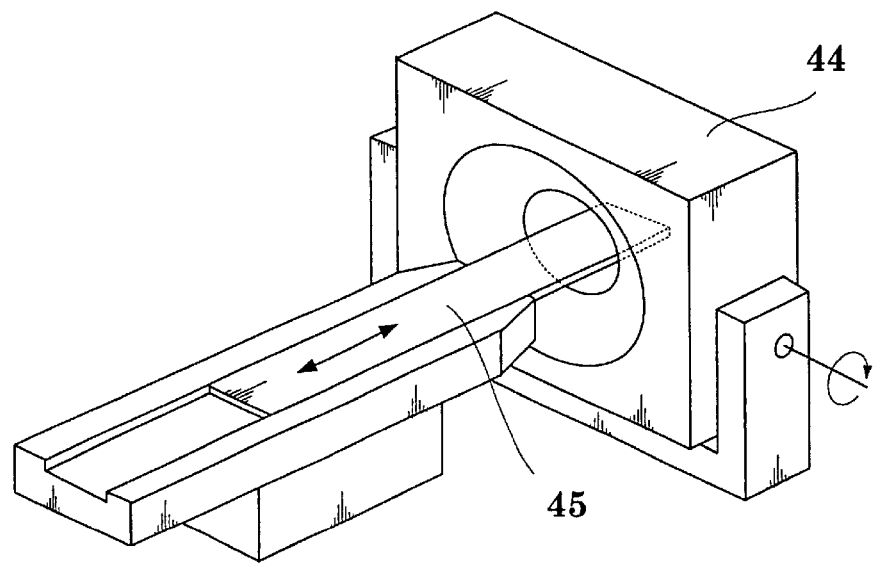
FIG. 4B is a schematic perspective view showing an outward appearance of the image pickup station shown in FIG. 4A.

An X-ray CT apparatus for medical use will be described as an X-ray radiographic apparatus implementing the image pickup station 40. This X-ray CT apparatus for medical use basically has the construction of the above X-ray radiographic apparatus. In particular, the image pickup station 40 is constructed as shown in FIG. 4. FIG. 4A is a schematic view of an image pickup station of the X-ray radiographic apparatus for medical use. FIG. 4B is a schematic perspective view showing an outward appearance of the image pickup station shown in FIG. 4A. A gantry 44 shown in FIG. 4A includes an X-ray tube 41 and an X-ray detector 42 arranged opposite each other to be revolvable together about the body axis (perpendicular to the plane of FIG. 4A) of a patient M placed on a top board 45. The X-ray tube 41 corresponds to the radiation source of this invention. The X-ray detector 42 corresponds to the detector of this invention.

In time of radiography by this apparatus, the input unit 10 is operated to determine, before picking up images of a region of interest of patient M, the number of views indicating how many times radiography should be performed while revolving the X-ray tube 41 and X-ray detector 42. Assuming that the number of views is 1800, radiography is completed by accumulating in the image processor 60 X-ray transmission data acquired in scan positions (i.e. projection positions) at intervals of 0.2 degrees of a full 360-degree revolution (=360 degrees/1800). The X-ray transmission data corresponding to 1800 lines is subjected to various correction processes to make radiographic data. This data is subjected to an FBP filtering process to obtain back projection data s. A sectional image is obtained by projecting the back projection data s 1800 times to back projection points in a two-dimensional section reconstruction area B set to the region of interest on a section intersecting the body axis of patient M.

Figure 6:
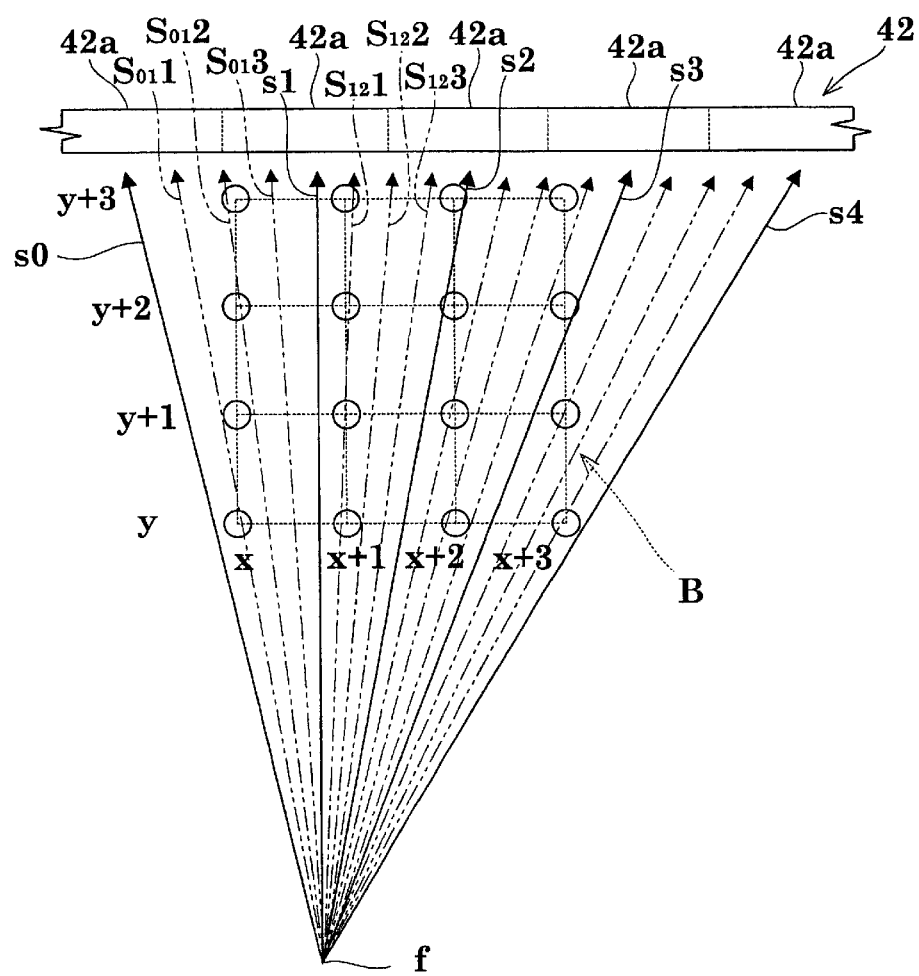
FIG. 6 is a schematic view illustrating a back projection of the back projection data enlarged by interpolation to a two-dimensional reconstruction area by a reconstruction method according to this invention.

FIG. 6 shows a relationship between projection and back projection for one of the above 1800 times. A straight line, which linkes an X-ray focus f of X-ray tube 41 and the center of each X-ray detecting element 42a of X-ray detector 42, represents a course of an X ray. The X-ray is emitted from the X-ray focus f and transmitted through the patient M in the reconstruction area B, and detected as X-ray projection data at the center of X-ray detecting element 42a of X-ray detector 42. Each arrow indicates a direction of projection. The direction opposite to the arrow direction is a direction of back projection. Back projection is effected in the direction from the center of each X-ray detecting element 42a to the X-ray focus f. These straight lines represent back projection data corresponding to the X-ray detecting elements among the back projection data s, which will be called hereinafter back projection data s0, s1, s2, s3 and so on. The two-dot chain lines in FIG. 6 represent enlarged interpolation data, which is generated by enlarging the back projection data by m=4 times by interpolation, and which will be called hereinafter data $S_{01}0$ to $S_{01}3$. Note that, in this embodiment for the m=4 times enlargement, data s0 is equal to enlarged interpolation data $S_{01}0$. This invention is characterized by a back projection of such enlarged interpolation data. This feature will particularly be described by dividing it into "Procedure 1" for enlarged interpolation data and "Procedure 2" for back projection.

"Procedure 1" is one for generating enlarged interpolation data by enlarging the back projection data by m times by interpolation. In this embodiment, enlarged interpolation data S(j) at each scan position is computed point by point by linear interpolation between two points widely used and from the following equation (5):

$$S(j)=\alpha \times (s(u+1)-s(u))+s(u) \qquad (5)$$

where u=INT (j/m) and α=j/m−u.

Computations for u and α in equation (5) above include divisions which are time-consuming. However, as a computing technique where m is a constant as in this invention, a division 1/m is first performed once to obtain M (=1/m), and a multiplication j/m=j×M is performed, as in the following equation (6), to shorten computation time;

$$S(j)=\alpha \times (s(u+1)-s(u))+s(u) \quad (6)$$

where M=1/m, u=INT (M×j) and α=M×j-u.

Details of computational complexity for one point of enlarged interpolation data based on equation (6) above are as follows, and a computational complexity of nine steps in total is necessary:

M×j floating point multiplication of coordinates ... one step

M×j→u making floating decimals of coordinates into integers ... one step u+1 adding integer to coordinates ... one step s (u), s (u+1) reading back projection data ... two steps α=t-u floating point computation of coordinates ... one step floating point multiplication of data ... one step floating point addition of data ... two steps In Procedure 1, the computation for enlarged interpolation data of one point is repeated with equation (6). First, enlarged interpolation data (m×L points) corresponding to each scan position is derived from back projection data of L points corresponding to each scan position. Further, computations are performed for all projection times (Np). From all the back projection data (L×Np points) corresponding to all scan positions, all enlarged interpolation data (m×L×Np points) is derived to complete Procedure 1. Thus, the computational complexity of Procedure 1 becomes 9×m×L×Np steps. This computational complexity is shown in the column "equation (6) enlarged interpolation in Procedure 1" in FIG. 7. While an example of linear interpolation between two points has been described, a spline interpolation may be adopted instead of the linear interpolation between two points.

Where m is an integer as in this embodiment, computations is performed at high speed by transforming an ordinary interpolation computation as expressed by equation (6) above. That is, where m is an integer, the spacing between two points is equally divided by m. Computations is performed as by the following equation (7) transformed for computation for every m points:

$$S(j)=S_{u, u+1}i=s(u)+SS \times i \quad (7)$$

where j=m×u+i, i=0, ..., m-1, SS=(s (u+1)-s (u))/m.

Further, with a program in which an order of solving equation (7) is fixed, the product sum computation of SS×i is made an addition of SS. Computations is performed fast in the order shown below as developed:

$$S(m \times u+0)=S_{u, u+1}0=s(u) \quad (8a)$$

$$S(m \times u+1)=S_{u, u+1}1=S_{u, u+1}0+SS \quad (8b)$$

$$S(m \times u+2)=S_{u, u+1}2=S_{u, u+1}1+SS \quad (8c)$$

$$S(m \times u+3)=S_{u, u+1}3=S_{u, u+1}2+SS \quad (8d)$$

Figure 5:
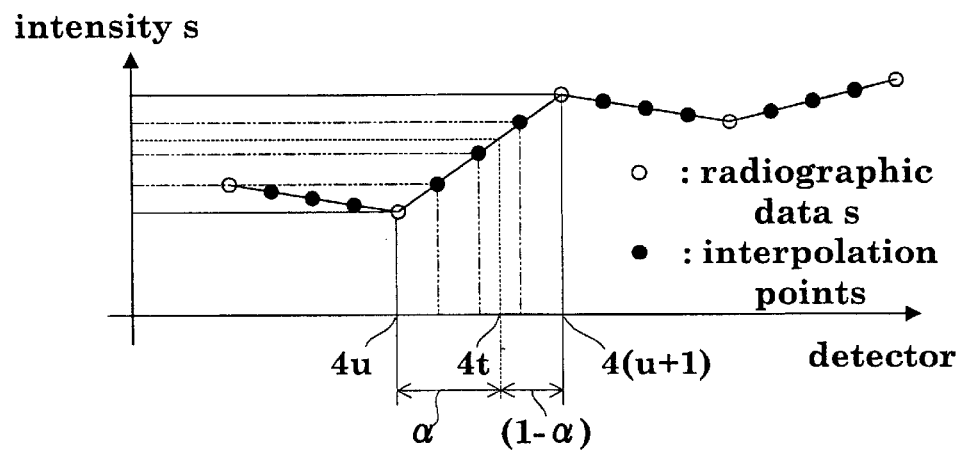
FIG. 5 is a schematic view showing back projection data enlarged by four times by interpolation.

$S_{01}1$, $S_{01}2$ and $S_{01}3$ shown in FIG. 6 represent enlarged interpolation data derived in this way. FIG. 5 shows numerical values of these enlarged interpolation data. In FIG. 5, the points shown in white circles are part of back projection data for each scan position in all projections. Interpolation computations are performed to enlarge the spacing between two adjacent points of the back projection data by m=4 times to derive three new data points shown in black circles in FIG. 5. Interpolation computations when i=0 result in s(u) which is back projection data itself. For the purpose of interpolation computation, this is not distinguished but the back projection data shown in white circles and new data points shown in black circles are collectively called enlarged interpolation data.

"Procedure 2" for back projection will be described next. Data is projected back to each reconstruction point (back projection point) b from among the enlarged interpolation data array S(j) corresponding to each scan position generated in "Procedure 1" described above. This back projection will be described with reference to FIG. 6. Conventionally, values derived from interpolation computations such as of data s0 and s1 are added to point b. In this invention, data $S_{01}1$ and so on already enlarged by interpolation in Procedure 1 is added in back projection to point b. To back projection point b (x, y), for example, interpolation data $S_{01}1$ is closer and more appropriate than data s0. Thus, interpolation data $S_{01}1$ is added in back projection to point b. To another back projection point b (x, y+1), interpolation data $S_{01}2$ is closer and more appropriate than interpolation data $S_{01}1$, and therefore is added in back projection to this point. To a further back projection point b (x, y+2), interpolation data $S_{01}2$ is closer and more appropriate than interpolation data $S_{01}1$, and is added in back projection to this point. To back projection point b (x, y+3), interpolation data $S_{01}2$ is closer and more appropriate than interpolation data $S_{01}3$, and is added in back projection to this point. In this way, enlarged interpolation data is added in back projection also to the other back projection points in the reconstruction area B.

"Procedure 2" is expressed by the following equation (9) as a back projection corresponding to each scan position represented by p:

$$b(x, y)=b(x, y)+S(j) \quad (9)$$

where j=INT (m×t (x, y, p)).

Function "t (x, y, p)" is a function for computing original data coordinates for back projection by floating point as in the prior art. Function "INT ( )" is a function for rounding off to integers. One feature of this invention resides in that a product of the rate of enlargement m and t is calculated before rounding off to integers.

The computational complexity of equation (9) above is as follows:

m×t floating point multiplication for multiplying coordinates by m=4 ... once m×t→j fourfold coordinates to integers ... once S(j) read and write ... once In the above computations in three steps, data to be added to b (x, y) is read, then b (x, y) is read, and floating point additions and subtractions are performed to complete one back projection for a certain scan position. Subsequently, b (x, y) is written. This makes computations performed six times in total. This computational complexity is shown in the column "equation (9) (1BP)" in FIG. 7.

This back projection is repeated the number of times of projection Np for the reconstruction area B of the size n×n to complete Procedure 2 and obtain a sectional image. The computational complexity for the entire reconstruction by this Procedure 2 becomes n×n×Np, which is shown in the column "equation (9) ALL (all BPs)" in FIG. 7.

Thus, the computational complexity for the back projection of a two-dimensional sectional image computed in Procedure 1 and Procedure 2 in this embodiment is 9×L× m×Np+6×n×n×Np as shown in the column "equation (6)+

(9) ALL (all computational complexity)" in FIG. 7. In this embodiment, all enlarged interpolation data is first computed in Procedure 1, and then all back projections are carried out in Procedure 2. Instead, the computations in Procedures 1 and 2 is performed for one scan position p after another, in which case the computational complexity remains the same.

To show a specific difference in computational complexity between this embodiment and the prior art, a ratio in the number of steps is computed as follows:

(equation (4) ALL in the prior art)/(equations (5)+(6) in the embodiment)

$$=(9 \times n \times n \times Np)/(9 \times L \times m \times Np + 6 \times n \times n \times Np)$$

$$=(9 \times n \times n)/(9 \times L \times m + 6 \times n \times n)$$

Since normally L=n, $$=(9 \times n \times n)/(9 \times n \times m + 6 \times n \times n)$$

$$=(9 \times n)/(9 \times m + 6 \times n) \quad (10)$$

From the above equation (10), when m=n×3/9, the embodiment and the prior art are the same in back projection computing speed seen in the number of steps. In this embodiment in which m=4, when n>12, the number of steps is less and the computations is performed faster than in the prior art. When n=512, the ratio in the numbers of steps derived from equation (10) is 1.48, hence 48% faster. Although an actual high-speed feature of this invention is dependent upon a DSP or CPU used, a faster speed exceeding this ratio in the number of steps can be achieved. Particularly, it is a great advantage that the number of radiographic data read in time of back projection is halved.

Next, the levels of reconstruction precision of the embodiment and the prior art will be described. Where the rate of enlargement m=infinite, obviously the computations are the same as in the prior art. A finite rate of enlargement m will cause errors. However, by giving a suitable value to the enlargement-rate m, images of excellent quality is reconstructed and such reconstructed images present no problem. For example, reconstructed images in the embodiment and those in the prior art have been compared in which the images are reconstructed from radiographic data acquired with an X-ray detector 42 having X-ray detecting elements 42a the number L of which is 512. The number of images radiographed, Np, is 1800, with a point object present at the center of reconstruction, and a circular object in a position a half radius away from the center of reconstruction (i.e. in a halfway position from the center to an edge of reconstruction). In the reconstructed images in the prior art, both the point object and circular object appear clearly with no moire pattern in the background (i.e. in the areas other than the point object and circular object). On the other hand, in the embodiment, when m=1, both the point object and circular object appear clearly, which are no less clear than in the prior art, but moire patterns in the background stand out. Next, when m=4 in the embodiment, both the point object and circular object appear clearly, no less clear than in the prior art, with little moire patterns in the background. It has been confirmed that these reconstructed images are equal to those in the prior art, excellent in quality and free from problem. Thus, by giving a suitable value to the rate of enlargement m, images of excellent quality is reconstructed, presenting no problem, with an excellent effect that section reconstruction computations is performed in a short time.

The embodiment and the prior art will be compared below in two-dimensional CT and focusing on the interpolating computational complexity which is an outstanding difference therebetween. In the prior art, back projection data is projected Np times back to the n×n pixels in the section reconstructing area B, and thus a total number of interpolating computations=n×n×Np. In the embodiment, on the other hand, back projection data is projected Np times back to the n×n pixels in the section reconstruction area B after enlarging all the back projection data by m times by interpolation, and thus a total number of interpolation computations=m×n×Np. Consequently, the number of times of interpolation is reduced to m×n times/n×n times=m/n in two-dimensional CT reconstruction, thereby to perform the section reconstruction computations in a short time.

The above embodiment uses a section reconstruction method for causing the image processor 60 (computer) to generate enlarged interpolation data by interpolating the back projection data, and then to perform back projection computations for projecting the enlarged interpolation data back to the two-dimensional reconstruction area B virtually set to the region of interest of patient M. The number of interpolation computations is reduced to an amount corresponding to the enlargement by interpolation of the back projection data. Thus, a fast radiographic apparatus is realized for reducing the reconstruction computation time.

By setting the rate of enlargement by interpolation of the back projection data to four times or more, an excellent quality of reconstructed images is secured, and the number of interpolation computations is reduced in proportion to the rate of enlargement (four times or more) by interpolation of the back projection data, to shorten the section reconstruction computation time.

This invention is not limited to the above embodiment, but modified as follows:

(1) In the foregoing embodiment, the enlargement-rate for enlarging the back projection data by interpolation is set to m=4. The enlargement-rate may be set to an integer or decimal of 1.0 or more. Particularly, in the case of rate 1.0, the number of interpolation computations becomes a minimum to shorten the section reconstruction computation time.

Figure 8:
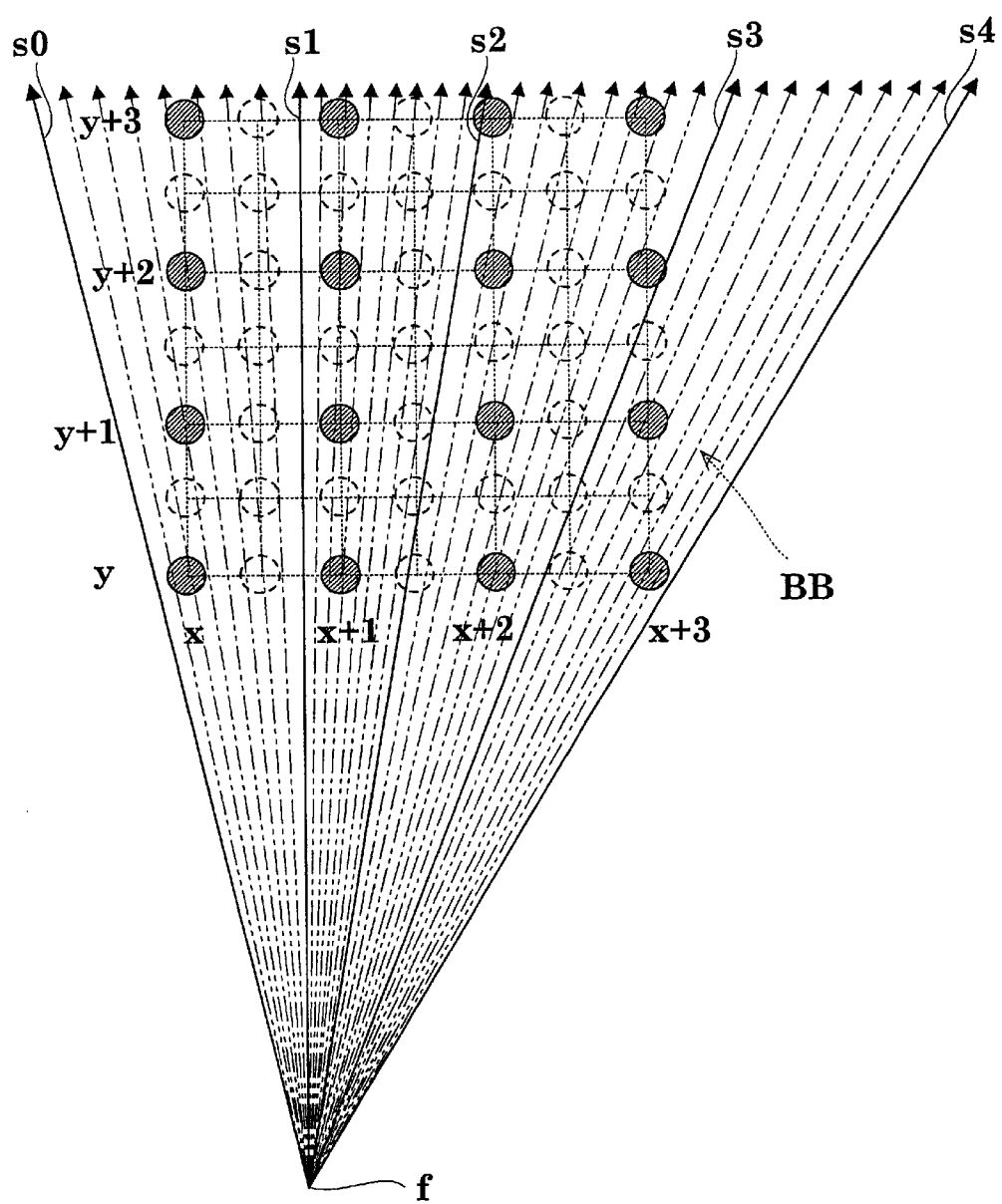
FIG. 8 is a schematic view illustrating a back projection to an enlarged reconstruction area.

(2) The reconstruction area B in the foregoing embodiment is a "real-size reconstruction area" in which the pitch of reconstruction points corresponds to the pitch of X-ray detecting elements 42a (pixels) of X-ray detector 42 divided by a geometric magnification (=distance from the focus of X-ray tube 41 to the X-ray detector 42/distance from the focus of X-ray tube 41 to the center of revolution). The invention set out in claim 4 is effective for an enlarged reconstruction area corresponding to the reconstruction area B enlarged by k times, with the pitch of back projection points set to 1/k. FIG. 8 is a schematic view showing an example of enlarged reconstruction area BB with 2n×2n back projection points formed by multiplying the reconstruction area B with n×n back projection points by k=2. In FIG. 8, the hatched circles represent the original back projection points (i.e. the above n×n back projection points in the reconstruction area B), and the broken line circles represent back projection points added to form the enlarged reconstruction area BB. In this enlarged reconstruction, the back projection data is enlarged by interpolation at a rate m' variable in proportion to the rate k of enlarged reconstruction. In the example shown in FIG. 8, the rate of enlargement m'=k×m=2×4=8 time. This maintains image quality equal to that provided by the "real-size reconstruction" at m=4.

The number of back projection points in the enlarged reconstruction area BB is four times (=k×k) the number of back projection points in the real-size reconstructing area B. In the conventional method, the number of interpolation computations also increases by four times, thereby considerably extending the reconstructing computation time. With this invention, however, the number of interpolation computations in Procedure 1, greatly reduced from that in the conventional method, is only doubled. This produces also an effect of substantially reducing the enlarged reconstruction computation time from that in the conventional method.

(3) The image pickup station 40 in the foregoing embodiment includes an X-ray tube 41 for irradiating the object or patient M with X rays in a fan beam, and a one-dimensional X-ray detector 42. The image pickup station 40 may include the X-ray tube 41 for irradiating the object M with X rays in a fan beam, and a varied two-dimensional area detector such as an image intensifier or flat panel X-ray detector revolvable synchronously with the X-ray tube 41, to carry out three-dimensional radiography. In a section reconstruction according to a conventional method of three-dimensional radiography, two-dimensional back projection data obtained by filtering two-dimensional radiographic data acquired in each scan position is projected three-dimensionally back to a three-dimensional reconstructing area virtually set to a region of interest of patient M. Where, for example, two-dimensional back projection data (n×n pixels) is projected Np times back to a three-dimensional reconstruction area (n×n×n pixels), interpolation computations must be performed as many as n×n×n×Np times.

When a three-dimensional reconstruction is performed as set out in claim 5 hereof, enlarged two-dimensional interpolation data ((m×n)×(m×n) pixels) is generated by enlarging two-dimensional back projection data (n×n pixel) by m times by interpolation in two directions, and thereafter the enlarged two-dimensional interpolation data is projected Np times back to a three-dimensional reconstructing area (n×n×n pixels). The number of interpolations=(m×n)×(m×n)×Np. Thus, the number of interpolations is decreased to m×m/n compared with the conventional method, to achieve high speed. These two-dimensional interpolation computations are performed often by using four adjacent points, and each interpolation computation itself takes time. Thus the decrease in the number of interpolation computations provides a significant advantage.

The above modification relates to a three-dimensional reconstruction based on an interpolation made in two directions. This invention is effective also for a three-dimensional reconstruction based on an interpolation made only in one direction. When interpolating only in one direction, enlarged two-dimensional interpolation data (n×(m×n) pixels) is generated by enlarging two-dimensional back projection data (n×n pixel) by m times by interpolation in one direction, and thereafter the enlarged two-dimensional interpolation data is projected Np times back to a three-dimensional reconstruction area. The number of interpolations=n×(m×n)×Np. Thus, the number of interpolations is decreased to m/n compared with the conventional method, to achieve high speed. The two-dimensional interpolation computations are performed often by using four adjacent points, and each interpolation computation itself takes time. On the other hand, the interpolating computation in one direction is a two-point interpolation. This produces an effect more than the decrease in the number of interpolation computations, to achieve high speed. Where images are reconstructed by enlarging data only in the important direction along Z-axis in a three-dimensional reconstruction area, sectional images smoothly connected along Z-axis may be obtained fast.

(4) In the foregoing embodiment, the rate of enlargement m for enlarging the back projection data by interpolation has a fixed value (e.g. m=4 times), regardless of directions of back projection. The enlargement-rate may be varied with directions of back projection as set out in claim 6.

Figure 9:
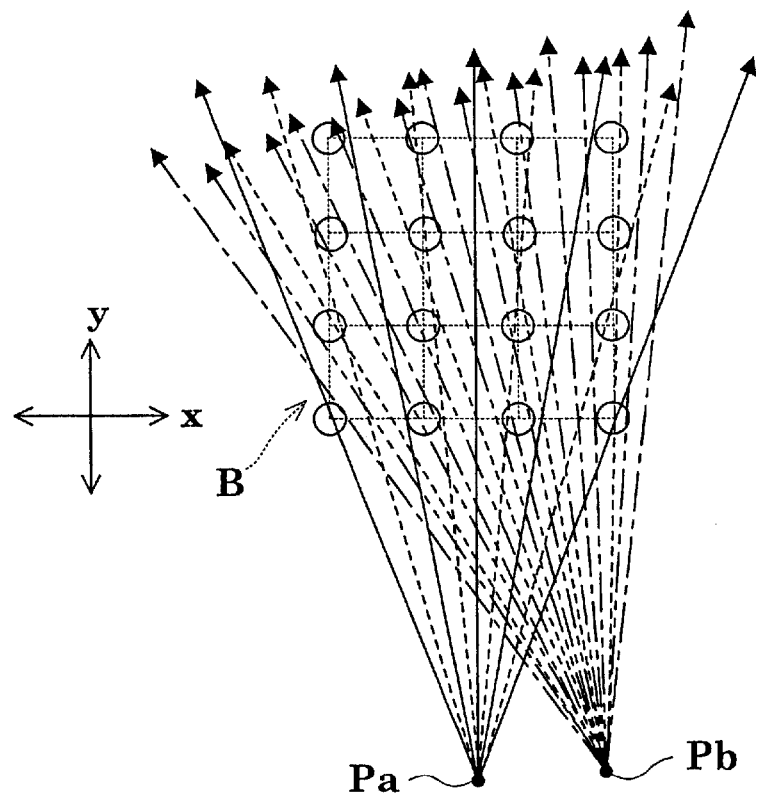
FIG. 9 is a schematic view illustrating variations in interpolation magnification of back projection data according to the direction of back projection.

Assume that, as shown in FIG. 9, for example, the X-ray tube 41 is at points Pa and Pb relative to the reconstructing area B. When the X-ray tube 41 is at point Pa, the directions of back projection are substantially parallel to the arrangement of pixels (back projection points) in the reconstruction area B. The back projection data is projected back with a rate of interpolation m=2. In FIG. 9, the broken lines indicate interpolation data interpolating, by m=2 times, the data shown in solid lines. Next, when the X-ray tube 41 is at point Pb, the directions of back projection are far from parallel to the arrangement of pixels (back projection points) in the reconstruction area B. That is, the directions of back projection are diagonal to the arrangement of pixels (back projection points) in the reconstruction area B (e.g. inclined by a maximum of 45 degrees relative to the x and y directions). The back projection data is projected back with a rate of interpolation m=4. In FIG. 9, the two-dot chain lines indicate interpolation data interpolating, by m=4 times, the data shown in one-dot chain lines.

Figure 10:
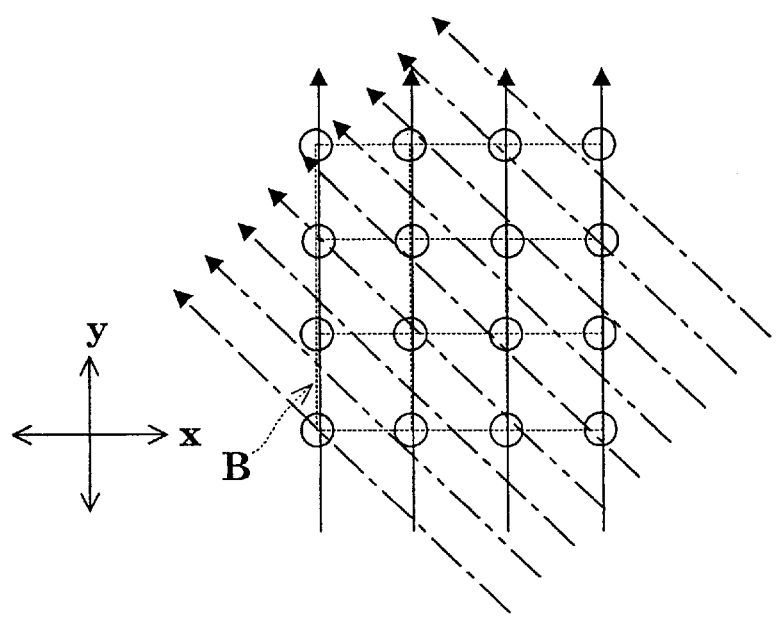
FIG. 10 is a schematic view illustrating variations in interpolation magnification of back projection data according to the direction of back projection in time of parallel beam reconstruction.

The invention set out in claim 6 will be described further with reference to a parallel beam reconstruction shown in FIG. 10. When the direction of back projection corresponds to the y direction as shown in solid lines in FIG. 10, the direction of back projection is parallel to the arrangement of back projection points in the reconstruction area B, and therefore no interpolation is required. However, when the direction of back projection is inclined by 45 degrees relative to the x and y directions as shown in two-dot chain lines in FIG. 10, the direction of back projection does not agree with the arrangement of back projection points in the reconstruction area B, and therefore the data needs to be interpolated. Data indicated by the one-dot chain lines is used as interpolated with data indicated by the two-dot chain lines in FIG. 10.

In the two examples described above, with variations in the direction of back projection, the pitch of reconstruction pixels seen from the direction of back projection also varies. Thus, the rate of enlargement for enlarging the back projection data by interpolation is varied according to the directions of back projection, to avoid deterioration in the quality of a reconstructed image due the directions of back projection.

Figure 11:
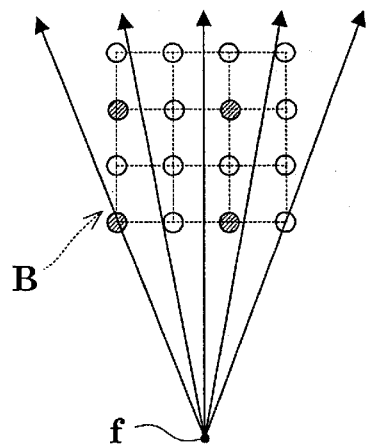
FIG. 11 is a schematic view illustrating a back projection to a reduced reconstruction area.

(5) The foregoing embodiment employs a "real-size reconstruction". When it is desired to know reconstruction results quickly, a reduced reconstruction may be performed with a reduced number of reconstruction points (back projection points). In the "real-size reconstruction area", the pitch of reconstruction points corresponds to the pitch of X-ray detecting elements 42a (pixels) of X-ray detector 42 divided by a geometric magnification (=distance from the focus of X-ray tube 41 to the X-ray detector 42/distance from the focus of X-ray tube 41 to the center of revolution). In the reduced reconstruction, the reconstruction area B is reduced to 1/k, with the pitch of reconstruction points increased by k times. FIG. 11 is a schematic view showing a reduced reconstruction area, based on k=2, with half the back projection points in the real-size reconstruction area B. Of the n×n back projection points in the real-size reconstruction area B, only the hatched circles represent the back projection points.

The white circles represent the points of no back projection (i.e. back projection points reduced out). The data projected back to these points are reduced out to lower the quality of reconstructed image. Then, the invention set out in claim 7 is applied to such a reduced reconstruction to avoid the deterioration in image quality. That is, the back projection data S is subjected to a moving average process, and thereafter average interpolation data enlarged by m times by interpolation is projected back to the reduced reconstruction area.

Figure 12:
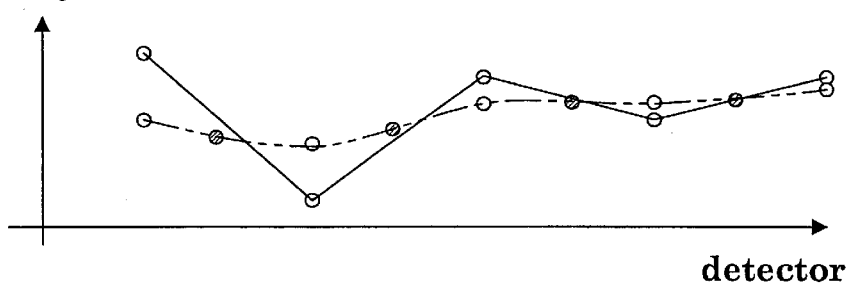
FIG. 12 is a schematic view illustrating an interpolation of back projection data by moving average.
Figure 13:
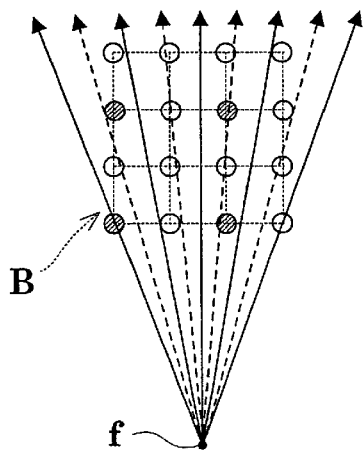
FIG. 13 is a schematic view illustrating a back projection of the back projection data interpolated by moving average to the reduced reconstruction area.

FIG. 12 shows an example of computing average interpolation data. The white circles on the solid line represent original back projection data. The white circles on the two-dot chain line represent back projection data after the moving average process. The hatched circles on the two-dot chain line represent average interpolation data given an interpolation by double. These moving average data are projected back to the reduced reconstruction area as shown in FIG. 13. Thus, the invention set out in claim 7 allows a reduced reconstructed image to be known quickly while avoiding deterioration in the quality of the reconstructed image.

(6) The section reconstruction method and radiographic apparatus in the foregoing embodiment are applicable to a medical CT apparatus for treating human patients M, or a radiographic apparatus for causing an X-ray tube and an X-ray detector to scan an object M synchronously (e.g. in a linear movement) to project a given point of the object M constantly to a predetermined point on the X-ray detector. The section reconstruction method and radiographic apparatus are applicable also to a nondestructive inspecting apparatus for inspecting printed circuits and various other electronic devices.

(7) In the foregoing embodiment, the X-ray tube irradiates the object M with X rays. The invention is not limited to the use of X rays. Electromagnetic waves penetrating the object M, such as gamma rays, light and electron beams, may also be used to produce similar effects. Thus, the radiographic apparatus according to this invention is not limited to X-ray radiographic apparatus, but is applicable also to all radiographic apparatus for performing radiography by using electromagnetic waves, other than X rays, penetrating the object M.

The present invention may be embodied in other specific forms without departing from the spirit or essential attributes thereof and, accordingly, reference should be made to the appended claims, rather than to the foregoing specification, as indicating the scope of the invention.

What is claimed is:

1. A section reconstruction method for projecting radiographic data of an object acquired in each scan position back to a section reconstruction area, said method comprising the step of:

generating enlarged interpolation data by interpolating back projection data and then projecting said enlarged interpolation data back to a two-dimensional or three-dimensional reconstruction area virtually set to a region of interest of said object, said back projection data being radiographic data, or data resulting from filtering of said radiographic data, said radiographic data being acquired in each scan position by causing a radiation source and a detector arranged opposite each other across said object to scan said object synchronously, or to scan said object synchronously with rotation of said object, said radiation source irradiating said object with electromagnetic waves capable of penetrating said object, said detector detecting electromagnetic waves transmitted through said object.

2. A section reconstruction method as defined in claim 1, wherein said enlarged interpolation data is generated by an enlargement-rate set to an integer or decimal of at least 1.0.

3. A section reconstruction method as defined in claim 1, wherein said enlarged interpolation data is generated by an enlargement-rate set to at least four times.

4. A section reconstruction method as defined in claim 1, wherein, when said reconstruction area is an enlarged reconstruction area subdivided to have pixel density exceeding a detector pixel density, said enlarged interpolation data is generated by an enlargement-rate variable in proportion to an enlargement-rate of an enlarged reconstruction.

5. A section reconstruction method as defined in claim 1, wherein, when a three-dimensional reconstruction is performed for projecting two-dimensional back projection data to the three-dimensional reconstruction area, two-dimensional enlarged interpolation data is generated by interpolating said two-dimensional back projection data, and said two-dimensional enlarged interpolation data is projected back to said three-dimensional reconstruction area.

6. A section reconstruction method as defined in claim 1, wherein said back projection data is enlarged by interpolation by an enlargement-rate variable with directions of back projection.

7. A section reconstruction method as defined in claim 1, wherein, when said reconstruction area is a reduced reconstruction area reduced to have pixel density less than a detector pixel density, average interpolation data generated by interpolation after taking a moving average of said back projection data is projected back to said reduced reconstruction area.

8. A section reconstruction apparatus for projecting radiographic data of an object acquired in each scan position back to a reconstruction area, said apparatus comprising:

a radiation source for irradiating said object with electromagnetic waves capable of penetrating said object;

a detector for detecting electromagnetic waves transmitted through said object; and image processing means for generating enlarged interpolation data by interpolating back projection data and then projecting said enlarged interpolation data back to a two-dimensional or three-dimensional reconstruction area virtually set to a region of interest of said object, said back projection data being radiographic data, or data resulting from filtering of said radiographic data, said radiographic data being acquired in each scan position by causing said radiation source and said detector arranged opposite each other across said object to scan said object synchronously, or to scan said object synchronously with rotation of said object.

9. A section reconstruction apparatus as defined in claim 8, wherein said enlarged interpolation data is generated by an enlargement-rate set to an integer or decimal of at least 1.0.

10. A section reconstruction apparatus as defined in claim 8, wherein said enlarged interpolation data is generated by an enlargement-rate set to at least four times.

11. A section reconstruction apparatus as defined in claim 8, wherein, when said reconstruction area is an enlarged reconstruction area subdivided to have pixel density exceeding a detector pixel density, said enlarged interpolation data is generated by an enlargement-rate variable in proportion to an enlargement-rate of an enlarged reconstruction.

12. A section reconstruction apparatus as defined in claim 8, wherein, when a three-dimensional reconstruction is performed for projecting two-dimensional back projection data to the three-dimensional reconstruction area, two-dimensional enlarged interpolation data is generated by interpolating said two-dimensional back projection data, and said two-dimensional enlarged interpolation data is projected back to said three-dimensional reconstruction area.

13. A section reconstruction apparatus as defined in claim 8, wherein said back projection data is enlarged by interpolation by an enlargement-rate variable with directions of back projection.

14. A section reconstruction apparatus as defined in claim 8, wherein, when said reconstruction area is a reduced reconstruction area reduced to have pixel density less than a detector pixel density, average interpolation data generated by interpolation after taking a moving average of said back projection data is projected back to said reduced reconstruction area.

* * * * *